United States Patent [19]

Varwig

[11] Patent Number: 4,772,740

[45] Date of Patent: Sep. 20, 1988

[54] ETHANOLAMINE SALT OF N-NITROSOPHENYLHYDROXYLAMINE AND INHIBITING POLYMERIZATION THEREWITH

[75] Inventor: John W. Varwig, St. Louis, Mo.

[73] Assignee: Mallinckrodt, Inc., St. Louis, Mo.

[21] Appl. No.: 708,313

[22] Filed: Mar. 5, 1985

[51] Int. Cl.$^4$ .................... C07C 67/62; C07C 51/50; C07C 111/00

[52] U.S. Cl. .................... 560/4; 252/186.25; 562/598; 564/112; 585/4

[58] Field of Search ............... 560/4; 252/186, 186.25; 564/112, 280; 562/598; 585/4

[56] References Cited

U.S. PATENT DOCUMENTS

| | | | |
|---|---|---|---|
| 2,954,314 | 9/1960 | Metzger et al. | 564/112 X |
| 3,344,135 | 9/1967 | Middleton | 260/239 |
| 3,413,349 | 11/1968 | Bertsch et al. | 564/112 |
| 3,426,063 | 2/1969 | Gros | 260/666.5 |
| 3,959,358 | 5/1976 | Jurisch | 560/4 X |
| 4,210,493 | 7/1980 | Stewart et al. | 203/8 |
| 4,310,676 | 1/1982 | Schropp | 560/4 |

FOREIGN PATENT DOCUMENTS 1064845 4/1967 United Kingdom .

OTHER PUBLICATIONS

Chemical Abstracts, vol. 100, No. 24, Jun. 11, 1984, p. 2, No. 192330K, (Zhang et al.), "Study on the Polymerization Inhibitors of Isoprene".

Primary Examiner—Werren B. Lone
Assistant Examiner—Vera C. Clarke
Attorney, Agent, or Firm—R. J. Klostermann; L. N. Goodwin; Veo Peoples

[57] ABSTRACT

The ethanolamine salt of N-nitrosophenylhydroxylamine ("NPHA") is effective as a polymerization inhibitor for ethylenically unsaturated monomers. The ethanolamine salt can be prepared by reacting ethanolamine with the ammonium salt of NPHA. Advantageously, the ethanolamine salt is soluble in high concentrations in water and a variety of polar organic solvents.

35 Claims, No Drawings

ETHANOLAMINE SALT OF N-NITROSOPHENYLHYDROXYLAMINE AND INHIBITING POLYMERIZATION THEREWITH

This invention relates to the ethanolamine salt of N-nitrosophenylhydroxylamine, solutions thereof and inhibiting polymerization therewith.

BACKGROUND OF THE INVENTION

Gros, U.S. Pat. No. 3,426,063, discloses a process for inhibiting thermal polymerization and/or the growth of popcorn polymer in compositions containing polymerizable ethylenically unsaturated hydrocarbons and/or esters in which there is admixed therein an N-nitrosoarylhydroxylamine or, preferably, a salt thereof. N-nitrosophenylhydroxylamine is among the specific compounds which are disclosed to be especially preferred. Examples given of salts of the N-nitrosoarylhydroxylamine which may be employed include the ammonium salts and, in some instances, "organic amine salts of the acidic tautomeric form of the N-nitrosoarylhydroxylamine . . . , the organic radicals of which each may contain 1–20 and preferably 8–16 carbon atoms." Gros discloses that, usually, the ammonium salts are water soluble and thus may be preferred for use in aqueous systems; while, on the other hand, unspecified "certain amine salts" are very soluble in the hydrocarbon monomer and thus may be preferred for use in all-monomer systems or organic solvent solutions of monomers. Gros specifically discloses that an organic solvent solution of cupferron (the ammonium salt of N-nitrosophenylhydroxylamine) or "the" amine salt of N-nitrosophenylhydroxylamine ma be added to an all-monomer system.

Although cupferron is an effective polymerization inhibitor, it has not been entirely satisfactory from a number of standpoints, including its limited solubility and limited storage stability. Cupferron is typically added to monomers such as acrylic acid in miniscule amounts (e.g. from about 20 to 200 parts per million (ppm) parts of monomer). To facilitate control over the addition in such miniscule amounts, users generally prefer to add cupferron as a liquid solution thereof in an amount of solvent which are acceptable for a given use. The acceptable amounts and types of solvent are dependent upon the particular application.

Although water is an acceptable solvent for introducing cupferron into systems containing acrylic acid where water is either present or permissible, water is not acceptable in appreciable amounts in final distillation steps in the manufacture of glacial acrylic acid nor in acrylate esters.

Acrylate esters may have acceptably introduced into them an alcohol, especially the particular alcohol from which the ester is derived, and accordingly an alcohol may be employed as solvent for adding cupferron to such esters in some instances. However alcohols, including the alcohol from which the ester is derived, are generally undesirable in the final purification stages of such esters due to the risk of co-distillation of the ester and the alcohol and resulting product contamination. It is generally unacceptable to admix methanol or other alcohols with acrylic acid in industrial facilities for the manufacture thereof due to the risk of esterification of the acid.

In general, users of cupferron require liquid solutions thereof in which the ratio of solvent to cupferron is low, e.g. 10:1 or less. Achieving a low ratio requires a solvent in which cupferron is highly soluble, e.g. in an amount of at least 10% for the ratio not to exceed 10:1. All parts, percents and other amounts setforth herein are by weight, unless otherwise indicated. Ratios lower than 10:1 (requiring solubilities of more than 10%) would be preferable.

Unfortunately, cupferron has limited solubility in selectively acceptable solvents such as water and lower alcohols (e.g. methanol etc.). Cupferron has the following limits of solubility at 25° C. in the indicated solvents: water (12%), methanol (5.5%) and isopropanol (0.38%), while it is essentially insoluble in hydrophobic solvents i.e., solvents which are immiscible with water). As a result of the limited solubilities of cupferron in the foregoing solvents therefor, objectionably large amounts of these solvents are required in many applications where cupferron would otherwise be a desirable inhibitor.

Solutions of cupferron, e.g. aqueous solutions thereof, are not entirely stable and undergo degradation in the presence of air, as manifested by discoloration and formation of a black precipitate. Minimizing the extent and rate of degradation requires, in practice, storing such solutions under an inert atmosphere such as nitrogen.

The various above-mentioned deficiencies of cupferron solutions are not overcome by the organic amine salts of N-nitrosoarylhydroxylamine disclosed in the above-cited Gros patent. On the contrary, organic aliphatic amine salts of N-nitrosophenylhydroxylamine (hereinafter sometimes referred to as NPHA) are unsatisfactory for use in inhibiting polymer formation in acrylic acids and acrylate esters. In the presence of such monomers, the amine salts decompose with formation of the organic aliphatic amines (e.g. ethylamine, etc.). The lower boiling amines (e.g. the $C_1$ to $C_7$ aliphatic amines) formed by decomposition of the corresponding amine salts create a substantial risk of co-distillation thereof with the acrylic acid or acrylate ester monomers being purified by distillation and resulting discoloration of polymers prepared from the monomers, such as, for example, poly(acrylic acid), poly(methyl methacrylate) and poly(ethyl acrylate). The higher boiling amines (e.g. the $C_8$–$C_{20}$ aliphatic amines) formed upon decomposition of the corresponding amine salts are so immiscible with water that such salts are not entirely satisfactory for addition to water-containing acrylic acid systems.

Accordingly there is a substantial need in the art for a salt of N-nitrosophenylhydroxylamine which is both (a) highly soluble in solvents which can suitably be added to acrylic acid and acrylate ester systems and (b) effective for inhibiting undesired formation of polymer in such systems.

DESCRIPTION OF THE INVENTION

A compound has now been found which substantially fulfills the above-mentioned need.

Generally stated, in one aspect of the present invention there is provided the ethanolamine salt of N-nitrosophenylhydroxylamine (i.e. the ethanolamine salt of NPHA).

In another aspect, this invention provides an aqueous solution of the ethanolamine salt of NPHA.

In yet another aspect, this invention provides a solution of the ethanolamine salt of NPHA in a solvent comprising ethanolamine.

In still another aspect, the present invention provides a solution of the ethanolamine salt in an alcohol which may be, for example, methanol, ethanol, n-propanol, isopropanol, n-butanol or 2-ethylhexanol.

In yet another aspect, this invention provides a method for inhibiting formation of undesired polymer from acrylic acids and esters thereof, which comprises adding thereto the ethanolamine salt of NPHA in an amount effective for inhibiting the formation of such polymer.

DETAILED DESCRIPTION OF THE INVENTION AND OF THE MANNER AND PROCESS OF MAKING AND USING IT

The ethanolamine salt of N-nitrosophenylhydroxylamine is sometimes hereinafter referred to as EA-NPHA or terms of similar import. The salt, EA-NPHA, can be prepared by reacting ethanolamine with cupferron in a suitable solvent for the reactants and, preferably, sparging the reaction system with nitrogen or other inert gas to aid in removing the ammonia which evolves in the course of the reaction. In general, suitable solvents include polar organic solvents capable of dissolving ethanolamine. Alcohols are preferred, and isopropanol is especially preferred for use as the reaction solvent. Preferably, the ethanolamine is initially dissolved in the reaction solvent and thereafter cupferron is added to the resulting solution with stirring. In general, cupferron is added in an approximately stoichiometric amount, i.e., in an amount such that a total of approximately one mole of cupferron is added per mole of ethanolamine. However, cupferron may be added in an amount less than stoichiometric (e.g., 0.9 mole) or in a molar excess (e.g., up to about 1.5 moles) per mole of ethanolamine. The reaction may be carried out under any suitable conditions, including a temperature of, for example, about 0° C. or less to slightly below the lowest decomposition temperature of the reaction system components (i.e., ethanolamine, cupferron and the solvent) or the lowest boiling point at the pressure employed of the system components, whichever is lower. Conveniently, the reaction may be carried out at room temperature (e.g., about 20°-25° C.) and at atmospheric pressure (e.g., 760 mm Hg absolute). The time required to complete the reaction is dependent upon the particular solvent employed, reaction temperature, and the relative amounts of reactants and solvent. In general, the reaction may be complete in from about 0.1 hour to about 5 hours or less (e.g., about 1 hour). The resulting EA-NPHA can be recovered using wellknown recovery methods. Recovery may be effected, for example, by cooling the reaction mixture to about 0° C. to crystallize the EA-NPHA, followed by any suitable liquid-solid separation procedure (e.g., filtration or centrifuging) or evaporating the solvent and any residual unreacted ethanolamine from the reaction mixture. Recovery is preferably effected by means of crystallization unless otherwise indicated. Preferably, crystallization is aided by seeding the cooled reaction mixture with a previously formed EA-NPHA crystal or other suitable seed.

The amount of the ethanolamine which may be employed in the above solvent reaction mixture is limited only by the solubility of the ethanolamine in the particular solvent. Such reaction is preferably carried out employing 12-18 parts of ethanolamine per 100 parts of isopropyl alcohol as the solvent.

EA-NPHA has been found to be an effective inhibitor of undesired polymerization such as thermal polymerization and popcorn polymer formation in ethylenically unsaturated acids and esters, such as acrylic acids and esters thereof. It is effective for inhibiting undesired polymerization in both liquid phases and vapor phases. That is, inhibition can be effected in liquid phases of such monomers, as well as in the vapor spaces above such liquid phases.

EA-NPHA advantageously has solubility in water and a variety of polar organic solvents. Accordingly, EA-NPHA offers substantial improvements over cupferron in that EA-NPHA is soluble in a variety of selectively acceptable solvents in amounts well in excess of 10%. The improvement of this invention is especially applicable for improvements in the manufacture of acrylic acids and esters thereof.

As used herein, the term "acrylic acids" includes substituted and unsubstituted acrylic acid, e.g., acrylic acid per se, methacrylic acid and the like. Monomeric esters of such acids include, for example, esters thereof with a lower alkanol having from 1 to about 8 carbon atoms, such as the methyl, ethyl, isopropyl, butyl, and octyl (e.g., 2-ethylhexyl) alcohols.

EA-NPHA is soluble in the following exemplary solvents, which are applicable to acrylic acid and acrylate ester monomers, in the indicated approximate amounts at approximately 20° C.: water (67%), methanol (56%), ethanol (34%), isopropanol (10%), butanol (10%), and 2-ethylhexanol (5%). In addition, EA-NPHA is soluble at approximately 20° C. in ethanolamine in amounts up to about 75%.

The various solutions can be prepared simply by admixing at any suitable temperature (e.g., about 20°-25° C.) this new salt compound in the selected solvent therefor.

Solutions of EA-NPHA in an aqueous solvent system (e.g., water alone) can suitably be added to monomer-including systems such as those including the acrylic acids (e.g., acrylic acid and methacrylic acid) in which water is either already present or permissible. Since the EA-NPHA solution being added to such monomers may contain up to the full limit of solubility, e.g., 67% of the inhibitor salt in water at 20° C., the inhibitor compound can be introduced into the monomer-containing system with substantially lower amounts of water than are required for cupferron. This is a significant advantage of great benefit in the acrylics industry. Similar advantages result from this invention by use of solutions of EA-NPHA in alcohols for use in adding EA-NPHA inhibitor to acrylate ester monomers or solutions thereof. Preferably, the alcohol employed as solvent for the EA-NPHA is the same as the alcohol from which the ester is derived by esterification of such alcohol with a desired acrylic acid (e.g., acrylic acid per se or methacrylic acid). Due to the low solubility of cupferron in alcohols from which acrylate esters are derived on a commercially important scale, this invention accordingly provides a significant advantage of great benefit in the acrylate ester industry. As in the case of water solutions of EA-NPHA, highly concentrated liquid solutions of an NPHA derivative and the associated advantages thereof are now available to the acrylate ester industry for inhibiting undesired polymerization of the esters. Since cupferron is essentially insoluble, if soluble at all, in alcohols such as isopropanol, n-butanol, and 2-ethylhexanol, an inhibiting amine salt of NPHA is now, for the first time, available as a solution in such alcohols for addition to monomer systems including the corresponding esters.

Various stages of the commercial processes for preparing glacial (i.e., anhydrous) acrylic acid wherein cupferron solutions have not been acceptable, can now have a solution of an amine salt of NPHA effectively and advantageously introduced for inhibition of undesired polymerization. This significant development is achieved by use of the ethanolamine (EA) solution of EA-NPHA provided by this invention. Unlike most $C_1$-$C_7$ alkyl amines which are released upon decomposition of NPHA salts including such alkyl amines as cationic moieties, ethanolamine does not present any substantial risk of codistillation with acrylic acids as in the final purification distillation steps employed in commercial practice for purifying such acids. Accordingly, by virtue of this invention, these and other stages in the commercial production of acrylic acids are now for the first time provided the benefits of an amine salt of NPHA free of any appreciable risk of contamination of the product acid upon attempted purification by distillation.

EA-NPHA solutions within the scope of this invention also include solutions of such salt wherein a mixture of two or more of the foregoing solvents are employed in the solvent system. Such solvent systems include, for example, ethanolamine and water, as well as ethanolamine (EA) and a suitable lower alcohol, e.g., methanol, ethanol, butanol, 2-ethylhexyl alcohol and the like, and EA and an alkoxy alcohol, e.g. 2-butoxyethanol. Solutions of EA-NPHA in a solvent system comprising ethanolamine, either alone or in conjunction with one or more other solvents advantageously can be prepared without requring isolation of EA-NPHA by appropriate choice of the reaction medium for preparing the salt.

For example, a solution of EA-NPHA in ethanolamine (EA) can conveniently be prepared simply by reacting cupferron with ethanolamine by contacting cupferron with a stoichiometric excess of ethanolamine. In all pertinent respects, this reaction can be carried out in the same manner set forth above for reacting ethanolamine with cupferron in a solvent for the reactants, it being understood that cupferron is added to an amount of ethanolamine in excess of a molar ratio of 1:1 of ethanolamine to cupferron. Preferably, this reaction is carried out by adding cupferron in an amount of 100 parts by weight per 100 parts by weight of ethanolamine (corresponding to a mole ratio of ethanolamine to cupferron of 2.5:1). Conveniently, the reaction conditions may include and preferably do include a temperature of about 20°-55° C. (most preferably about 50° C.) and atmospheric pressure, as well as stirring of the reaction mixture and use of an inert gas to purge ammonia from the liquid reaction mixture. Such purging may be effected throughout the course of the reaction or upon completion thereof. This reaction is usually complete within about 3-5 hours. The resulting ethanolamine solution of NPHA can be used directly as an inhibitor solution without need for recovery of the EA-NPHA therefrom. If desired, the resulting solution may thereafter be admixed with compatible co-solvents for the EA and NPHA, such as the lower ester forming alcohols set forth above. However, where solutions containing, as the solvent system, ethanolamine and one or more of such co-solvents as water or the aforesaid alcohols, the solution is preferably prepared by carrying out an in situ reaction of cupferron with ethanolamine in a liquid system containing a stoichiometric excess of ethanolamine and the additional one or more co-solvents.

It is understood that EA-NPHA may, if desired, be introduced into, or otherwise admixed with, monomers or monomer-containing systems to be inhibited.

The EA-NPHA may be admixed with an all-monomer system or other monomer-containing system (e.g., aqueous or organic solutions of the monomer) employing any effective amount of EA-NPHA. Expressed on the basis of the amount of NPHA moiety in the EA-NPHA, effective amounts of the EA-NPHA are generally in the range of from about 20 to about 200 part per million parts of the monomer. It has been found that addition of such amounts of EA-NPHA to monomers or monomer-containing systems such as the acrylic acids and esters thereof effectively inhibits thermal polymerization of such monomers, while at the same time effectively inhibiting formation of popcorn polymer. Advantageously, the inhibiting effects achieved by introducing EA-NPHA into these monomers is observed in both the liquid phase and the vapor phase.

It is understood that this invention also embodies ethylenically unsaturated monomer compositions formed by the addition thereto of EA-NPHA, with and without a solvent therefor, the reaction product of the monomer and EA-NPHA, or, in combination, EA-NPHA and the reaction product in amounts effective for inhibiting undesired polymerization.

Practice of the present invention is illustrated by the following examples, which are given by way of illustration and not by way of limitation. As indicated above, all amounts throughout this disclosure are by weight, unless otherwise indicated.

Although the foregoing description has been given in terms of EA-NPHA, it is to be understood that good results may also be obtained with other alkanolamine salts of NPHA such as the diethanolamine salt of NPHA, the triethanolamine salt of NPHA, N,N-(dimethyl)ethanolamine salt of NPHA, the propanolamine salt of NPHA, the butanolamine salt of NPHA, and the corresponding alkanolamine salts of other N-nitrosoarylhydroxylamines such as N-nitroso-1-naphthylhydroxylamine (e.g., the ethanolamine salt of N-nitroso-1-naphthylhydroxylamine), and mixtures of two or more of such salts.

An especially preferred solution is that obtained by reacting cupferron with ethanolamine in the presence of water wherein the initial ratio of ethanolamine to water is 2:1 and the amount of cupferron added to the ethanolamine-water mixture is one part per 1 part of such mixture. Although it is not necessary for this reaction to go to 100% completion based on the amount of cupferron added, the reaction typically goes to substantial completion (i.e., at least about 95% or more).

EXAMPLE 1

This example illustrates the preparation and isolation of EA-NPHA. To a solvent mixture containing 17.1 grams of ethanolamine (EA) and 115 grams of isopropanol was added with stirring 43.2 grams of cupferron. The temperature of the system at the beginning of the addition of cupferron was about 20°-25° C. After the cupferron addition was completed, the reaction mixture was heated to a temperature of about 50°-53° C. and maintained thereat. Nitrogen was sparged into the liquid reaction mixture during the addition of the cupferron, thereby assisting in removing the ammonia released during the course of the reaction. Stirring was continued and the temperature was maintained at approximately 50°-53° C. for about two hours after the addition of cupferron was completed. It was observed that the solid phase (cupferron) had disappeared at the end of this two hour period. Next, heating was discontinued and the reaction mixture was allowed to slowly cool in air to about 20°-25° C. while stirring and nitrogen sparging were continued. Next, after standing undisturbed for about 16-20 hours, the desired crystallization occurred, resulting in the reaction mixture now appearing as a highly viscous slurry. Next, this slurry was transferred to a vacuum filter, where the solid product was recovered from the reaction mixture by vacuum filtration, followed by washing with hexane and drying. The resulting solid product (43.0 grams) was found to melt at 78°-81° C. IR and $H^1$ and $C^{13}$ NMR spectra confirmed that it was the ethanolamine salt of N-nitrosophenylhydroxylamine, i.e., EA-NPHA, which may be respresented by the following formula:

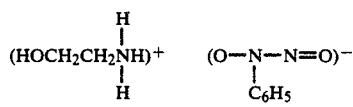

EXAMPLE 2

This example illustrates the in situ preparation of EA-NPHA in ethanolamine.

In a manner similar in all pertinent respects to that of Example 1 (including use of a glass vessel equipped with a stirrer, a source of heat and nitrogen sparge), 50 grams of cupferron were added in small increments to 50 grams of ethanolamine with stirring and warming to about 45°-50° C. Nitrogen was sparged into the liquid reaction mixture during the addition of cupferron and continued for 1-2 hours after the addition was complete, during which time the initially hazy reaction mixture became clear. Next, heating was discontinued but stirring and nitrogen sparging was continued while the clear reaction mixture was cooled to room temperature. The resulting solution contained approximately 46% by weight of EA-NPHA, expressed as the NPHA moiety, and based on method of preparation.

EXAMPLE 3

This example illustrates the preparation in situ of a solution of EA-NPHA in a mixture of ethanolamine and water as the solvent system.

The procedure of Example 2 was repeated in all pertinent respects except that the liquid medium employed was prepared by mixing 33.3 grams of ethanolamine with 16.7 grams of water. The resulting aqueous solution of EA-NPHA in the ethanolamine-water solvent system assayed approximately 49% of the salt, expressed as NPHA, and contained 13.9% water as determined by Karl Fisher analysis.

The various solutions referred to hereinafter containing EA-NPHA in mixtures of ethanolamine and alcohols were prepared substantially in the same manner as set forth in Example 3, except substituting the indicated alcohol for the water.

It will be appreciated that the procedures set forth in the foregoing examples may be employed to prepare solutions of different concentrations of EA-NPHA, and in the case of solutions composed of ethanolamine and additional solvents such as water and alcohols, the ratio of the additional solvent to ethanolamine can likewise be varied.

EA-NPHA and its solutions have been very good storage stability and can be stored for long periods of time without requiring an inert gas such as nitrogen, yet remain substantially free of discoloration.

EXAMPLE 4

Liquid Phase Test(s)

The efficacy of EA-NPHA as an inhibitor of undesired liquid phase polymerizations such as thermal polymerization and the growth of popcorn polymer, was determined in the following manner. A heat exchanger was constructed from ¼ inch O.D. stainless steel tubing about 4 feet in length curled into a coil of 3 circular loops. The loops of the coil were immersed in an oil bath at 150° C. and pressure gauges were operably connected at the inlet and outlet of the thus heated coil. Pressure buildup across the coil would reflect the degree of fouling in the tubing due to polymer formation in the heated coil: the greater the pressure differential, the greater the fouling. In addition, a stainless steel screen was incorporated in the recirculation line not in a position to affect the pressure differential through the heated coil. Polymer collected on this screen was dried and weighed.

Acrylic acid containing the substance undergoing testing was circulated sequentially through the heated coil, an external cooling coil and a recirculation line connected to the inlet of the heated coil. Two experiments were carried out for 100 hours. In the first experiment a solution of EA-NPHA in ethanolamine (containing 45% of EA-NPHA expressed as NPHA) was added to acrylic acid in an amount sufficient to provide 90 ppm, i.e., 90 parts of EA-NPHA (expressed as NPHA) per million parts of acrylic acid. In the second experiment phenothiazine (PTZ) was added in amount to provide 1000 ppm based on the acrylic acid. At the end of 100 hours the pressure differential across the heated coil was recorded. The data obtained are given in the following table:

| Inhibitor Added | Pressure Differential | Weight of Polymer Collected |
| --- | --- | --- |
| EA-NPHA (90 ppm) | 6 mm Hg | 0.7 grams (g.) |
| PTZ (1000 ppm) | 16 mm Hg | 1.8 grams (g.) |

Thus the EA-NPHA in ethanolamine solution was at least twice as effective as approximately 10 times as much PTZ in inhibiting the formation of polymer.

Vapor Phase Test(s)

Vapor phase inhibition of growth of popcorn polymer was determined using a system containing an oil-bath heated 1-liter round bottom flask equipped with a Vigreux column and provided with a vacuum source and a magnetic stirring device. A liquid mixture formed by adding, with stirring, to one hundred ml of acrylic acid a substance to be tested as an inhibitor of popcorn polymer formation and growth was added to the flask. A stainless steel mesh basket containing an accurately weighed kernel of styrene-butadiene rubber popcorn (0.01 to 0.02 gram) was suspended in the vapor phase above the liquid mixture. The liquid mixture was stirred and heated under reduced pressure. Reflux into the Vigreux column at a reduced pressure of about 50 mm Hg and a bath temperature of 95°–100° C. was carried out for 6 hours. At the end of this time the popcorn kernel was recovered, dried and weighed and the present change in popcorn kernel weight was calculated. No increase in weight of the kernel indicates complete inhibition of the growth of popcorn polymer in the vapor phase. Results of six tests are given in the following table, wherein the amounts of EA-NPHA and cupferron added to the acrylic acid as well as the concentration of solutions thereof are expressed as NPHA:

| Test | Substance Added (Amount) | % Weight Change of Popcorn Kernel |
|---|---|---|
| 1. | EA-NPHA, solid (89 ppm) | −2.2 (loss) |
| 2. | 45% EA-NPHA, ethanolamine solution (112 ppm) | +4.5 |
| 3. | 45% EA-NPHA, ethanolamine solution (99 ppm) | −1.4 (loss) |
| 4. | Cupferron, solid (102 ppm) | 0.0 |
| 5. | Cupferron, solid (102 ppm) | −4.8 (loss) |
| 6. | Phenothiazine (126 ppm) | +636. |

The results show that addition of EA-NPHA is very effective for inhibiting the growth of popcorn polymer in the vapor phase, whether it is added as a solid or as an ethanolamine solution. The inhibiting effect which results from addition of EA-NPHA is substantially better than obtained for phenothiazine and compares favorably with addition of cupferron.

Distillation Test(s)

To demonstrate that ethanolamine essentially does not co-distill with acrylic acid three distillation experiments were carried out. In one test, acrylic acid containing 500 ppm of phenothiazine was distilled at a temperature of 85° C. and a pressure of 85–90 mm of mercury (Hg) using a Vigreux column without packing. In the two other tests, ethanolamine was added to acrylic acid (containing 500 ppm of phenothiazine) in an amount of 1% by volume. The distillates were analyzed, in triplicate, for total nitrogen by the standard Kjeldahl procedure. The results are given in the following table:

| | Total Nitrogen, ppm |
|---|---|
| Acrylic Acid, Starting Material | 7, 4, 6 |
| Distillate Samples | |
| 1. 1% Ethanolamine added | 20, 7, 14 |
| 2. 1% Ethanolamine added | 14, 7, 14 |
| 3. No Ethanolamine added | 32, 4, 14 |

Within the precision of the analytical procedure employed, no evidence of ethanolamine carryover was found.

EXAMPLE 5

(A) Popbottle Test - Methyl Methacrylate

The efficacy of EA-NPHA as an inhibitor for acrylate esters is illustrated in this example.

Fifteen milliliters of methyl methacrylate were added to each of ten 60-milliliter popbottles. Ten micromoles of a substance to be tested were added to the ester and then the bottles were sealed. Half the bottles, one for each of the 5 substances, had been sparged with nitrogen before sealing. The bottles were then immersed in an oil bath at 85° C. and the thus heated bottles were observed at frequent intervals to determine the length of time required for the onset of polymerization. The data are shown below:

| | Time to Polymerize (Hours) | |
|---|---|---|
| Substance | Air | Nitrogen |
| EA-NPHA | 200 | No polymer at 1000 |
| Cupferron | 21 | 877 |
| Phenothiazine | 514 | 712 |
| Hydroquinone | 640 | 944 |
| None | 8 | 17 |

The data show that EA-NPHA is highly effective for inhibiting thermal polymerization of methyl methacrylate. Similar results are contemplated for other acrylate esters.

(B) Hanging Basket Test - Methyl Methacrylate

The procedure of the Vapor Phase Test section of Example 4 was repeated in all pertinent respects except as follows. Methyl methacrylate was substituted for the acrylic acid in an equal volumetric amount. The substances tested for popcorn polymer inhibition were EA-NPHA, cupferron, phenothiazine and hydroquinone. A unit portion of each substance was added initially and again after each elapsed hour until 6 unit portions were added. The EA-NPHA was added as a solution of 45% EA-NPHA, expressed as NPHA, in ethanolamine which was further diluted with sufficient water to lower the EA-NPHA concentration to approximately 10%, expressed as NPHA. The cupferron was added as a dilute aqueous solution containing approximately 10% cupferron, expressed as NPHA. The phenothiazine and hydroquinone were both added as approximately 10% solutions thereof in methyl methacrylate. The unit portions of the four solutions were of such amount that the amounts of the various substances added in each unit portion were as follows, per million parts of methyl methacrylate in the liquid mixture: 100 parts each of cupferron, phenothiazine and hydroquinone and that amount of EA-NPHA which is equimolar to 100 parts of cupferron.

| Substances Added | % Weight Gain of Popcorn Polymer Seed |
|---|---|
| EA-NPHA | 92 |
| Cupferron | 18 |
| Phenothiazine | 237 |
| Hydroquinone | 243 |

The data shows that EA-NPHA is highly effective for inhibiting growth of popcorn polymer in methyl methacrylate, substantially surpassing phenothiazine and hydroquinone and closely approaching cupferron in efficacy for this application.

EXAMPLE 6

This example illustrates the in situ preparation of the diethanolamine salt of NPHA in a mixture of diethanolamine and water as the solvent system. This salt is sometimes hereinafter referred to as DEA-NPHA.

In a manner similar in all pertinent respects to that of Example 1 (including use of a glass vessel equipped with a stirrer, a source of heat and nitrogen sparge), 10.5 grams of cupferron were added in small increments to 19.5 grams of a solvent mixture containing 11.7 grams of diethanolamine and 7.8 grams of water with stirring and warming to about 45° C. Nitrogen was sparged into the liquid reaction mixture during the addition of cupferron and continued for 5 hours after the addition was complete, during which time the initially hazy reaction mixture became clear. Next, heating was discontinued but stirring and nitrogen sparging was continued while the clear reaction mixture was cooled to room temperature. The resulting solution contained approximately 32% by weight of DEA-NPHA, expressed as the NPHA moiety, and based on method of preparation.

EXAMPLE 7

This example illustrates the preparation in situ of a solution of DEA-NPHA in a mixture of diethanolamine and water as the solvent system.

The procedure of Example 6 was repeated in all pertinent respects except that 9 grams of cupferron was added to 21 grams of a liquid medium prepared by mixing 12.6 grams of diethanolamine with 8.4 grams of water. The resulting solution of DEA-NPHA in the diethanolamine-water solvent system contained approximately 28% of the DEA-NPHA salt, expressed as NPHA.

EXAMPLE 8

This example illustrates the efficacy of DEA-NPHA for inhibiting thermal polymerization of acrylic acid.

Solutions of DEA-NPHA in a mixture of diethanolamine and water prepared as described in Examples 6 and 7 were each diluted with sufficient water to provide two solution, each containing 1% DEA-NPHA, expressed as NPHA.

Fifteen milliliters of acrylic acid were added to each of eight 60-milliliter popbottles. To the acrylic acid in each of three of the bottles (Nos. 1-3) was added a sufficient amount of the dilute solution based on Example 6 to provide an amount of added DEA-NPHA corresponding to 89 parts of NPHA per million parts of acrylic acid. This addition was repeated for three other bottles (Nos. 4-6) except that the dilute solution based on Example 7 was added. These six bottles were sparged with nitrogen, sealed, immersed in an oil bath at 120° C. and the thus heated bottles were observed at frequent intervals to determine the length of time required for the onset of polymerization.

Concurrently, for comparative purposes, the two other bottles were similarly treated except that, instead of adding a DEA-NPHA solution, to each of these two bottles (Nos. 7 and 8) was added a sufficient amount of 1% cupferron in water to provide an addition of 100 parts of cupferron per million parts of acrylic acid.

The data are shown below:

| Bottle No. | Time (Hours) To Onset of Polymerization |
|---|---|
| 1 | 65 |
| 2 | 65 |
| 3 | 113 |
| 4 | 65 |
| 5 | 113 |
| 6 | 113 |
| 7 | 65 |
| 8 | 65 |

Preferred ethanolamine solutions herein contain EA-NPHA in an amount from about 20 to about 55%, more preferably about 47%, expressed as NPHA (i.e., expressed in terms of the stoichiometric equivalent amount of NPHA).

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. The ethanolamine salt of N-nitrosophenylhydroxyylamine.
2. A solution comprising the salt of claim 1 in a solvent selected from the group consisting of water, polar organic solvents and mixtures thereof.
3. The solution of claim 2 wherein said solvent comprises water.
4. The solution of claim 3 wherein said solvent is water.
5. The solution of claim 4 wherein said salt is dissolved in an amount of up to about 67%.
6. The solution of claim 5 wherein said amount is at least 20%.
7. The solution of claim 2 wherein said solvent comprises ethanolamine.
8. The solution of claim 7 wherein said solvent is ethanolamine.
9. The solution of claim 8 wherein said salt is dissolved in an amount of up to about 75%.
10. The solution of claim 9 wherein said amount is at least 20%.
11. The solution of claim 10 wherein said amount is from 20% to about 55%.
12. The solution of claim 7 wherein said solvent further comprises water.
13. The solution of claim 12 wherein said solvent contains from about 1 to about 99 parts of water per 100 parts of the combined amount of water and ethanolamine.
14. The solution of claim 13 wherein said solvent is a mixture of water and ethanolamine.
15. The solution of claim 13 wherein said solvent further comprises an alcohol.
16. The solution of claim 2 wherein said solvent is an alcohol.
17. The solution of claim 7 wherein said solvent is mixture of ethanolamine and an alcohol.
18. A method for inhibiting formation of undesired polymer from an ethylenically unsaturated monomer selected from the group consisting of polymerizable ethylenically unsaturated acids, polymerizable ethylenically unsaturated esters and mixtures thereof, which comprises admixing an effective amount of the ethanolamine salt of N-nitrosophenylhydroxylamine with a composition comprising said monomer.
19. The method of claim 18 wherein a solution of said salt in a solvent comprising water is admixed with substituted or unsubstituted acrylic acid.
20. The method of claim 18 wherein a solution of said salt in a solvent comprising ethanolamine is added.
21. The method of claim 20 wherein said solution is admixed with a composition comprising glacial acrylic acid and said solvent is ethanolamine.

22. The method of claim 20 wherein said solvent further comprises water.

23. The method of claim 18 wherein a solution of said salt in a solvent comprising an alcohol is admixed with an ester of substituted or unsubstituted acrylic acid, said ester derived from said alcohol.

24. The method of claim 23 wherein said solvent further comprises ethanolamine.

25. The method of claim 23 wherein said ester is methyl methacrylate.

26. A composition comprising (a) an ethylenically unsaturated monomer selected from the group consisting of polymerizable ethylenically unsaturated acids and polymerizable ethylenically unsaturated esters and (b) a polymer-inhibiting amount of the ethanolamine salt of N-nitrosophenylhydroxylamine.

27. The composition of claim 26 wherein said monomer is substituted or unsubstituted acrylic acid or an ester thereof.

28. The composition of claim 27 wherein said acid is acrylic acid and said ester is methyl methacrylate.

29. The method of claim 19 wherein said substituted acrylic acid is methacrylic acid.

30. The method of claim 19 wherein said solution is admixed with a composition comprising acrylic acid.

31. The composition of claim 27 wherein said substituted acrylic acid is methacrylic acid.

32. The composition of claim 27 wherein said monomer is acrylic acid.

33. A method for inhibiting formation of undesired polymer from a polymerizable ethylenically unsaturated acid monomer, which comprises admixing an effective amount of the ethanolamine salt of N-nitrosophenylhydroxylamine with a composition comprising said acid monomer.

34. The method of claim 33 wherein said acid monomer is substituted or unsubstituted acrylic acid.

35. The method of claim 34 wherein said acid monomer is unsubstituted acrylic acid.

* * * * *